US00PP37266P2

(12) United States Plant Patent
Hansen

(10) Patent No.: US PP37,266 P2
(45) Date of Patent: Feb. 10, 2026

(54) ***HELIOPSIS* PLANT NAMED 'Rays for Days'**

(50) Latin Name: ***Heliopsis helianthoides* (L.) Sweet**
Varietal Denomination: Rays for Days

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/831,569

(22) Filed: Apr. 25, 2025

(51) Int. Cl.
*A01H 5/02* (2018.01)
*A01H 6/14* (2018.01)

(52) U.S. Cl.
USPC ..... Plt./437

(58) Field of Classification Search
USPC ..... Plt./437
See application file for complete search history.

*Primary Examiner* — Susan McCormick Ewoldt

(57) ABSTRACT

The new and distinct hardy perennial *Heliopsis* plant named 'Rays for Days' with dense, rounded, extensively-branched habit, strong, tall, upright stems that resist lodging. The foliage is medium green and broadly ovate to narrowly deltoid. Freely-flowering double inflorescences in a capitulum with multiple rows of golden-yellow, overlapping, ray florets beginning in early July and continuing for about 6 weeks. The new plant is useful in the landscape en masse, as an accent, in containers or as cut flowers.

1 Drawing Sheet

Botanical denomination: *Heliopsis helianthoides* (L.) Sweet.

Variety designation: 'Rays for Days'.

STATEMENT REGARDING PRIOR DISCLOSURES UNDER 37 CFR 1.77(B)(6)

The first offer for sale of *Heliopsis* 'Rays for Days' was to Pleasant Run Nursery by Walters Gardens, Inc. on Jun. 7, 2024. Walters Gardens, Inc. obtained the new plant and all information relating thereto, directly from the inventor. No plants of *Heliopsis* 'Rays for Days' have been sold, in this country or anywhere in the world, by any name, nor has any disclosure of the new plant been made more than one year prior to the filing date of this application, and such sale or disclosure within one year was either derived directly or indirectly from the inventor and would be a 35 U.S.C. § 102(b) exception.

BACKGROUND AND ORIGIN OF THE PLANT

The present invention relates to a new and distinct cultivar of *Heliopsis* 'Rays for Days'. The new plant was selected as a single seedling from the cross by the inventor between 'Sunny Disposition' (not patented) as the female or seed parent and a proprietary selection of the seed strain 'Bleeding Heart' (not patented) as the male or pollen parent on Aug. 1, 2020. Seed was harvested on Nov. 24, 2020, and eventually assigned the breeder code 20-13-1 toward the end of the trial period. 'Rays for Days' was approved in an initial evaluation in the summer of 2021 and slated for later introduction. The new plant was selected based on its compact habit, strong stems, ability to withstand lodging, mildew resistance, attractive colorful foliage, high-quality flowers over a long period, and ability to attract pollinators. The new plant has been asexually first propagated by division and later by shoot tip cuttings with the resultant asexually propagated plants remaining identical to the original plant, stable and true to type in successive generations.

SUMMARY OF THE INVENTION

Plants of the new False Sunflower have not been observed under all possible combinations of environmental conditions and cultural practices. The phenotype may vary somewhat with variations in environmental conditions comprising temperature, daylength, light intensity, and fertility, without, however, any variations in genotype.

The following traits have been repeatedly observed and are determined to be the unique characteristics of the new *Heliopsis* plant. These characteristics in combination distinguish 'Rays for Days' as a new and distinct *Heliopsis* plant:

1. Broadly ovate to narrowly deltoid, medium green foliage;
2. Dense rounded plant habit;
3. Extensive branching habit;
4. Very floriferous and freely flowering habit beginning in early July and continuing for about six weeks;
5. Double inflorescences with multiple rows of golden-yellow ray florets on compact stems;
6. Strong garden performance and excellent for cut flowers.

The female parent has variegated foliage green surrounding the veins and yellowish cream between the veins, and the inflorescences have fewer ray florets. The male parent has foliage that has purple tinting, a taller habit, and inflorescences with fewer ray florets of orangish red. The male parent has a taller less compact habit and the new flowers emerge intense orange red and mature to golden orange with red centers.

The following cultivars are the most similar cultivars known to the inventor: 'Asahi' (not patented), 'Double Sunstruck' U.S. Plant Pat. No. 26,608, and the seed variety 'Summer Sun' (not patented).

'Asahi' produces miniature inflorescences with a single outer row of ray florets and several inner layers of disk florets. 'Double Sunstruck' has weaker stems that have a greater tendency to lodge and the foliage is white between the veins. 'Summer Sun' has a slightly taller and narrower habit, and inflorescences have fewer rows of ray florets.

BRIEF DESCRIPTION OF THE DRAWINGS

The photographs of the new plant demonstrate the unique traits of *Heliopsis* 'Rays for Days' and the overall appearance of a three-year-old plant in the full sun display garden of a nursery in Zeeland, Michigan. The colors are as accurate as reasonably possible with color reproductions. Variation in ambient light spectrum, source and direction may cause the appearance of minor variation in color.

Figure 1:
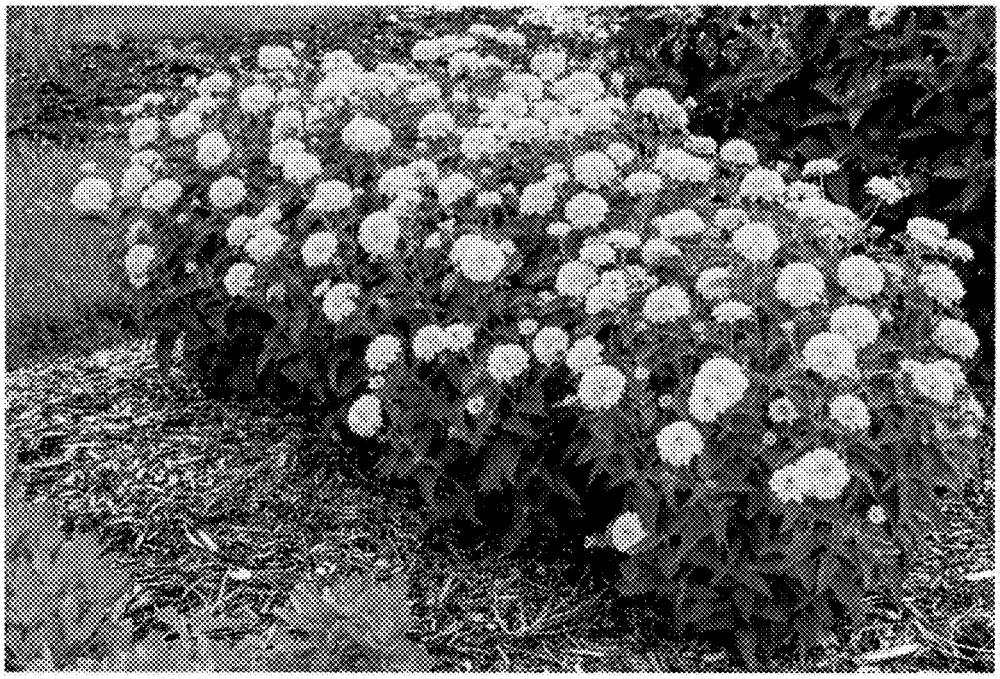
FIG. 1 shows the landscape habit of the new plant.
Figure 2:
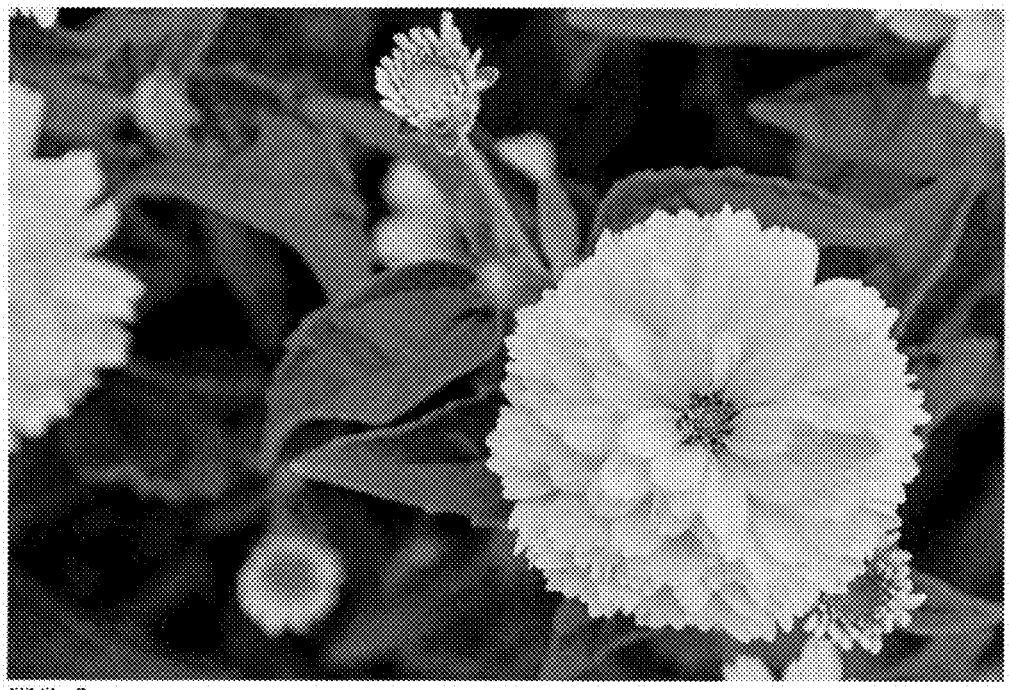
FIG. 2 shows a close-up of the inflorescence and bud.

DETAILED BOTANICAL DESCRIPTION.

The following descriptions and color references are based on the 2015 edition of The Royal Horticultural Society Colour Chart except where common dictionary terms are used. *Heliopsis* 'Rays for Days' has not been observed in all possible environments. The phenotype may vary slightly with different growing environments such as temperature, light, fertility, soil pH, moisture, and maturity levels, but without any change in the genotype. The following observations and size descriptions are based on three-year-old plants grown in a trial garden at a nursery in Zeeland, Michigan with supplemental fertilizer and water as needed and without growth regulators or pinching.

Botanical classification: *Heliopsis helianthoides;*

Parentage: The female (or seed) parent is 'Sunny Disposition'; the male (or pollen) parent is a seedling selection of 'Bleeding Hearts';

Plant habit: Multi-stemmed, heavily-branched, herbaceous perennial forming a dense rounded mound;

Propagation: Shoot tip cuttings;

Time to initiate roots: About one to two weeks;

Plant size: To about 75 cm tall and 92 cm wide;

Growth rate: Moderate; about 8 to 12 weeks to finish in a 3.8-liter container from a rooted 25 mm plug liner;

Root description: Fibrous; medium thickness; light tan to white in color, depending on soil composition, water quality, fertilizer type and formulation, substrate temperature, and physiological age of roots; medium density;

Stems: About 40 per plant; cylindrical; micro-puberulent; to about 66 cm length and 7 mm diameter at base;

Stem color: Proximally between RHS 146D and RHS 145A, distally between RHS 146D and RHS 145C, with the lowest internode nearest RHS 183B striated with nearest RHS 146D;

Branches: About 6 branches per stem beginning about 50 cm above soil; cylindrical; micro-puberulent; strong; flexible; at about a 30-degree angle away from main stem; to about 18 cm long and 2 mm diameter at base; color nearest RHS 146B;

Branch aspect: About 30 to 45 degrees above the horizon;

Nodes: About 7 below terminal flower; average internode length about 8 cm; node color between RHS 146D and RHS 145A;

Leaf description: Broadly ovate to narrowly deltoid; opposite; apex acute; base attenuate; margin micro-ciliolate and serrate with about 12 per side; scaberulose adaxial and abaxial;

Leaf size: To about 10 cm long and 6 cm wide, average about 8.5 cm long and 5 cm wide;

Leaf color: Young adaxial between RHS 143A and RHS 144A, young abaxial nearest RHS 146B; mature flowering stage adaxial between RHS 137A and RHS 137B;

Veins: Reticulate; slightly recessed and glabrous adaxial, abaxial micro-puberulent to scaberulose and costate;

Vein color: Young adaxial and abaxial midrib and primary veins between RHS 145C and RHS 146D and secondary veins both adaxial and abaxial between RHS 146D and RHS 145A; mature adaxial midrib and primary veins nearest RHS 146D and secondary veins nearest RHS 137B, mature abaxial midrib and primary veins between RHS 146D and RHS 145C and secondary veins nearest RHS 137B;

Petioles: Concavo-convex; sparsely puberulent adaxial and abaxial; to about 16 mm long and 5 mm across at base;

Petiole color: Adaxial and abaxial between RHS 146D and RHS 145C;

Inflorescence: In terminal capitulum; inflorescences semi-double with disk florets in the center and 90 to 110 ray florets in four to six layers surrounding about 50 disk florets; about 24 inflorescences per stem;

Flowering season: Begins in early July and continues for about six weeks;

Inflorescence buds: Tubular with flat top and rounded base; with ray florets still upright-about 20 mm tall and 20 mm across;

Bud color: Ray florets nearest RHS 3A;

Inflorescence longevity: Lasting about seven to ten days on the plant or as a cut flower; persistent;

Fragrance: Very slight, sweet;

Inflorescence size: To about 6.5 cm across and 4 cm tall;

Disk receptacle: Obconical with acute apex and flat base, about 7 mm across and 7 mm tall in maturity;

Receptacle color: Nearest RHS 155B as developing and nearest RHS 197C at maturity;

Ray florets: Ligulate; pistillate; about 90 to 110 ray florets in four to six imbricate whorls; lanceolate with bifid emarginate apex indented to about 1 mm to 2 mm; base attenuate to cuneate; margin entire; adaxial and abaxial surface glabrous and matte; with typically two longitudinal furrows; aspect outer whorls arcuate downward, and inner whorls horizontal to slightly upwardly when mature;

*Size*.—To about 32 mm long and 12 mm across near middle.

*Ray floret color*.—Upon initially becoming flat-adaxial proximal portion between RHS 17A and RHS 21A and distal portion nearest RHS 3A, abaxial nearest RHS 14A; near the final stage of effective inflorescence adaxial proximally nearest RHS 17B and distally nearest RHS 13A, abaxial between RHS 12A and RHS 12B.

*Disk florets*.—About 50 per inflorescence and arrangement in typical Fibonacci spirals; tubular with exserted anthers and style.

*Size*.—To about 7 mm long and 3 mm wide at expanded style.

*Corolla tube*.—Consisting of five indistinguishable perianth or tepals; to about 5 mm long and 2 mm wide at apex.

*Tepals*.—Acute apex; fused in basal 5 mm; margin entire; glabrous; slightly lustrous adaxial and abaxial; to about 5 mm long and about 0.7 mm across at fusion; color apex adaxial and abaxial distally nearest RHS 17B; proximally adaxial and abaxial nearest RHS 145D.

Reproductive organs: Ray florets anandrous;

*Gynoecium*.—To 8 mm long; exserted.

*Style*.—Cylindrical; to about 3 mm long and 0.2 mm diameter; color nearest RHS 17A.

*Stigma*.—Bifid in distal 2 mm; color nearest RHS 17A.

*Ovary*.—Obconical; about 3 mm long and 2 mm diameter at apex and about 1 mm diameter at base; color between RHS 145D and 145C.

Reproductive organs: Disk florets: perfect;

*Gynoecium*.—To 7 mm long; exserted.

*Style*.—Cylindrical; to about 2.5 mm long and 0.2 mm diameter; color nearest RHS 17A.

*Stigma*.—Bifid in distal 2 mm; color nearest RHS 17A.

*Ovary*.—2.5 mm long and 1 mm across; color between RHS 157D and RHS 156D.

*Androecium*.—Connate; to about 5 mm long.

*Anthers*.—Five; synandrous; introrse; basifixed; tube to about 2 mm long and 0.5 mm diameter; color between RHS N199A and RHS 199A.

*Filaments*.—Five; to about 3 mm long and 0.2 mm diameter; color nearest RHS 155C.

*Pollen*.—Abundant; color nearest RHS 21A.

Seeds: Achene; truncate apex; acute base; surface smooth, glabrous, matte; quadrangular distally; to about 3.5 mm long and 1.5 mm across at apex; about 15 per inflorescence; color nearest RHS N199B;

Flowering period: In Western Michigan beginning early July for about six weeks; individual florets remain open for about 4 to 6 days;

Flower attitude: Upwardly;

Phyllaries: About 21 per inflorescence in two whorls; lanceolate; acute apex; margin entire; puberulent and matte adaxial and abaxial; to about 9 mm long and 4 mm across at base;

Phyllary color: Adaxial between RHS N137B and RHS 137A; abaxial between RHS 146A and RHS 137B;

Peduncles: Cylindrical; micro-puberulent; strong; stiff; upright; to about 10 cm long, 4 mm diameter proximally, and 5 mm diameter at base of inflorescence;

Peduncle color: Nearest RHS 146D;

Growth: The new plant has been observed to have good garden performance and tolerance to high winds and strong rains.

Hardiness: Winter hardy in USDA zones 4 to 9;

Pest and disease susceptibility: Shows resistance to powdery mildew (*Neoerysiphe galeopsidis*) but shows no other resistance or susceptibility observed beyond that which is typical for *Heliopsis*.

I claim:

1. A new and distinct hardy perennial *Heliopsis* plant named 'Rays for Days' essentially as herein described and illustrated.

* * * * *